United States Patent
Swisher et al.

(10) Patent No.: US 10,369,083 B2
(45) Date of Patent: Aug. 6, 2019

(54) ADAPTER ASSEMBLY FOR ENTERAL FEEDING AND METHOD OF MAKING

(71) Applicant: KPR U.S., LLC

(72) Inventors: David Rork Swisher, St. Charles, MO (US); Michael Dorsey, Edwardsville, IL (US); Sandra Walker, St. Charles, MO (US)

(73) Assignee: KPR U.S., LLC, Mansfield, MA (US)

( * ) Notice: Subject to any disclaimer, the term of this patent is extended or adjusted under 35 U.S.C. 154(b) by 0 days.

(21) Appl. No.: 14/955,660

(22) Filed: Dec. 1, 2015

(65) Prior Publication Data

US 2016/0158110 A1    Jun. 9, 2016

Related U.S. Application Data

(60) Provisional application No. 62/086,385, filed on Dec. 2, 2014.

(51) Int. Cl.
| | | |
|---|---|---|
| *A61J 15/00* | (2006.01) | |
| *A61M 39/10* | (2006.01) | |
| *A61M 39/20* | (2006.01) | |

(52) U.S. Cl.
CPC .......... *A61J 15/0026* (2013.01); *A61M 39/10* (2013.01); *A61M 39/1011* (2013.01); *A61M 39/20* (2013.01); *A61J 2205/30* (2013.01); *A61M 2039/1033* (2013.01); *A61M 2039/1077* (2013.01); *A61M 2205/6018* (2013.01); *A61M 2207/00* (2013.01)

(58) Field of Classification Search
CPC .. A61M 2039/1094; A61M 2039/1077; A61M 39/10; A61M 39/20; A61M 2039/1033
See application file for complete search history.

(56) References Cited

U.S. PATENT DOCUMENTS

| | | | | |
|---|---|---|---|---|
| 5,057,093 A | * | 10/1991 | Clegg | A61M 39/10 128/912 |
| 5,267,983 A | * | 12/1993 | Oilschlager | A61J 15/0026 285/148.24 |
| 5,375,592 A | | 12/1994 | Kirk et al. | |
| 5,413,561 A | | 5/1995 | Fischell et al. | |
| 5,776,117 A | | 7/1998 | Haselhorst et al. | |
| 5,988,700 A | * | 11/1999 | Prichard | A61M 39/10 138/118 |
| 6,106,502 A | | 8/2000 | Richmond | |

(Continued)

FOREIGN PATENT DOCUMENTS

CA        866269 A        3/1971

OTHER PUBLICATIONS

International Search Report dated Feb. 10, 2016 in related International Application No. PCT/US2015/063187, 5 pages.

(Continued)

*Primary Examiner* — Nathan R Price
*Assistant Examiner* — John A Doubrava

(57) ABSTRACT

An adapter assembly includes a tapered connector including a central passage and a tapered outer surface for sealing with a tube or bottle. A male connector for connection to a female connector to fluidly communicate the female connector with the tube or bottle is coupled with the tapered connector. A method of forming such an adapter assembly is also disclosed.

11 Claims, 8 Drawing Sheets

(56) References Cited

U.S. PATENT DOCUMENTS

| | | |
|---|---|---|
| D454,637 S | 3/2002 | Nestenborg |
| D468,015 S | 12/2002 | Horppu |
| 6,609,520 B1 | 8/2003 | Carlsen et al. |
| D492,030 S | 6/2004 | Rani |
| D546,946 S | 7/2007 | Blake et al. |
| D561,329 S | 2/2008 | McMichael et al. |
| D638,933 S | 5/2011 | Hill et al. |
| D643,920 S | 8/2011 | Gil et al. |
| D654,166 S | 2/2012 | Lair |
| D655,000 S | 2/2012 | Mirigian |
| 8,864,736 B2 | 10/2014 | Knight |
| D734,456 S | 7/2015 | Cromett et al. |
| D737,436 S | 8/2015 | Lev et al. |
| 2004/0146341 A1 | 7/2004 | Sundheimer et al. |
| 2005/0245899 A1 | 11/2005 | Swisher |
| 2008/0277926 A1* | 11/2008 | Inman, Jr. ............. A61M 39/10 285/123.15 |
| 2010/0090456 A1 | 4/2010 | Halaczkiewicz et al. |
| 2010/0176584 A1* | 7/2010 | Ito .................. A61M 39/10 285/23 |
| 2013/0046272 A1* | 2/2013 | Knight ................ A61J 9/001 604/411 |
| 2013/0270819 A1* | 10/2013 | Amborn ............. A61M 39/10 285/328 |
| 2015/0032089 A1* | 1/2015 | Way .................. A63M 39/1011 604/535 |
| 2016/0206516 A1* | 7/2016 | Kunishige ............. A61J 15/00 |

OTHER PUBLICATIONS

Written Opinion of the International Searching Authority dated Feb. 10, 2016 in related International Application No. PCT/US2015/063187, 6 pages.

"Alternate Syringes: Low Displacement Option," Rork Swisher, ISO 80369 Series Meeting, Berlin, Germany, Mar. 19, 2014, 11 pages.

International Search Report and Written Opinion for Application No. PCT/US2015/063187, dated Feb. 10, 2016, 10 pages.

* cited by examiner

US 10,369,083 B2

ADAPTER ASSEMBLY FOR ENTERAL FEEDING AND METHOD OF MAKING

FIELD

The present disclosure generally relates to an adapter assembly for enteral feeding.

BACKGROUND

Tubing and catheter misconnections are a serious problem in hospitals. One such type of misconnection error involves enteral feeding tubes and intravenous catheters. Enteral feeding tubes are used to administer liquid nutritional solutions and medications directly to a patient's gastrointestinal system. In contrast, intravenous catheters are used to administer liquid nutritional solutions and medications directly to a patient's vascular system. Patients may be harmed if feeding solutions are administered intravenously and vice versa. Errors such as this occur because medical professionals use similar or identical tubing for different purposes. Enteral feeding connectors including a discriminating fitting help to ensure the proper fluid lines are connected for enteral feeding. Discriminating connectors may provide challenges for pharmacies and others who must fill syringes and other medical devices from containers not including the discriminating connection.

SUMMARY

In one aspect, an adapter assembly comprises a tapered connector including a central passage and a tapered outer surface for sealing openings of different sizes in at least one of a tube and a bottle. A male fitting is coupled with the tapered connector and in fluid communication with the central passage for attaching a device having a complementary female fitting to the tapered connector.

In another aspect, an assembly for use in producing an adapter assembly including a tapered connector having a tapered outer surface, the assembly comprises a male fitting and a connection member fixedly attached to the male fitting. The connection of the male fitting and connection member forms a fluid path through the male fitting and connection member. The connection member includes a mating portion adapted for mounting on the tapered connector. In some cases, the tapered connector is comprised of an elastomeric material, such as a resilient thermoplastic polymer having a hardness in a range of from about 35 to 75 Shore A hardness.

In yet another aspect, a method of forming an adapter assembly comprises providing a tapered connector including a central passage and a tapered outer surface for sealing with a tube or bottle. A subassembly is formed to include a male fitting connected to a mating member. The subassembly is coupled with the tapered connector by inserting the mating member of the subassembly into the central passage of the tapered connector thereby forming a sealing, interference fit with the tapered connector.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
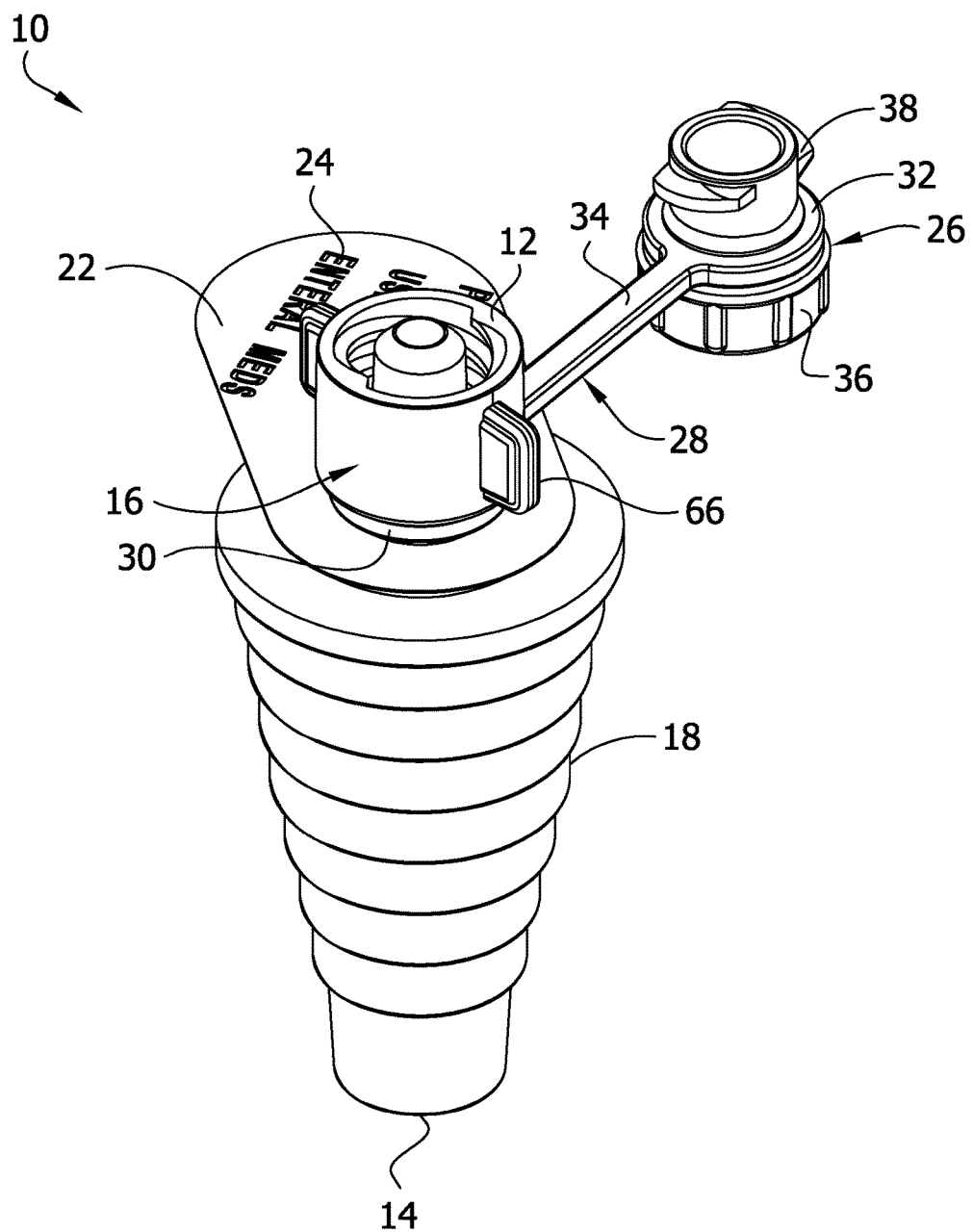
FIG. 1 is a schematic illustration showing a perspective view of an adapter assembly in accordance with one or more aspects of the present invention.

Referring to FIG. 1, an enteral feeding adapter assembly is generally indicated at 10. The adapter assembly is configured to fluidly connect an enteral feeding element (e.g., syringe, feeding bag, pump, etc.) to a fluid conduit or reservoir (e.g., medical tubing, bottle, etc.) for delivering fluid to a subject through the fluid conduit or retrieving fluid from the fluid reservoir. The adapter assembly 10 includes an enteral feeding element connection end 12 for connecting to an enteral feeding element (not shown) and a fluid conduit/reservoir connection end 14 for connecting to a fluid conduit/reservoir (not shown). As will be explained in greater detail below, the enteral feeding element connection end 12 may include a male fitting 16 for connecting to a complementary female fitting (not shown) associated with the enteral feeding element. The connection ensures that only a compatible enteral feeding connector can be connected to the adapter assembly 10. Thus, an incompatible connector, such as a luer-tip syringe cannot be properly connected to the adapter assembly. A female fitting (not shown) could alternatively be part of the adapter assembly for connecting to male fittings.

Figure 2:
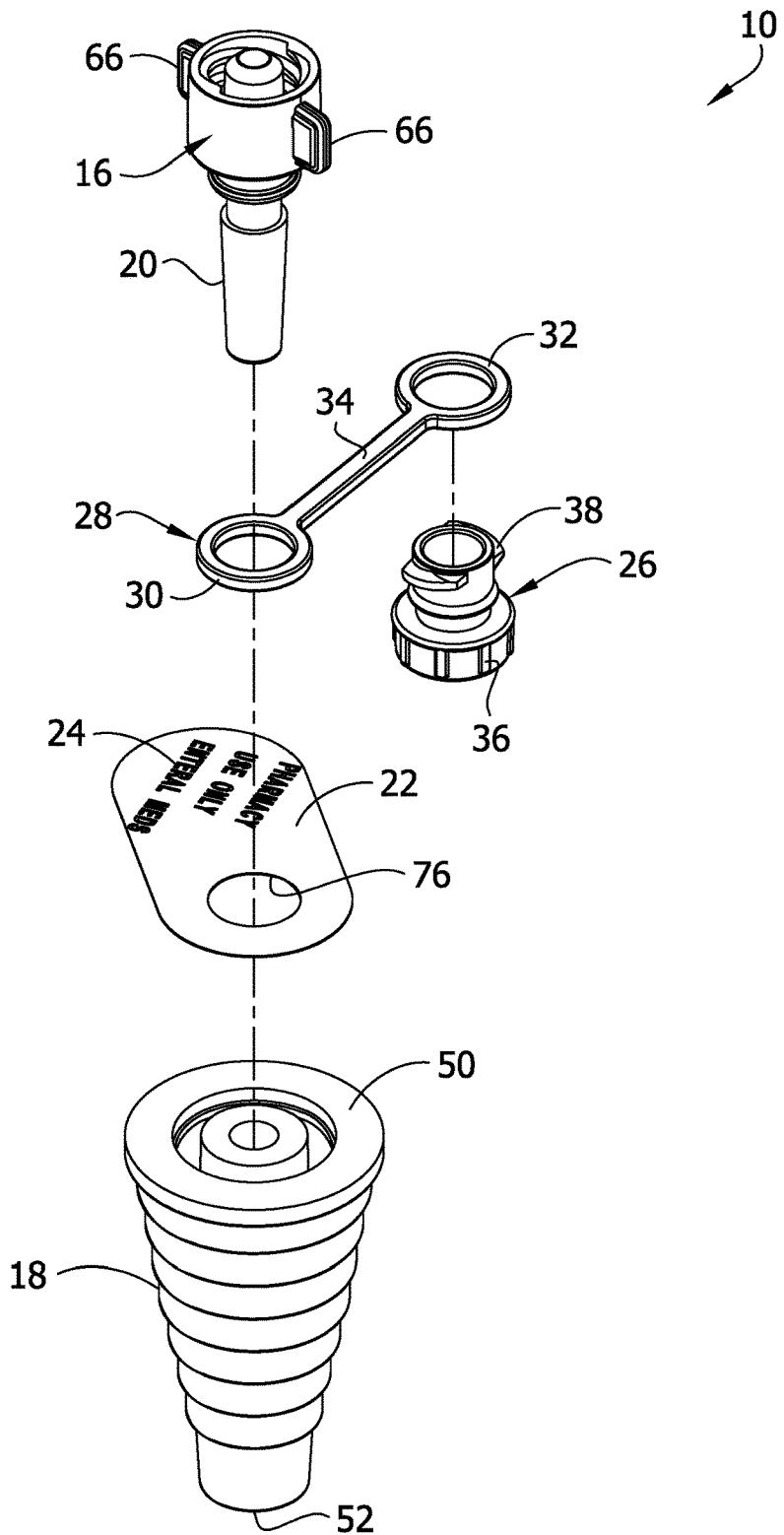
FIG. 2 is schematic illustration showing an exploded view of the adapter assembly.
Figure 3:
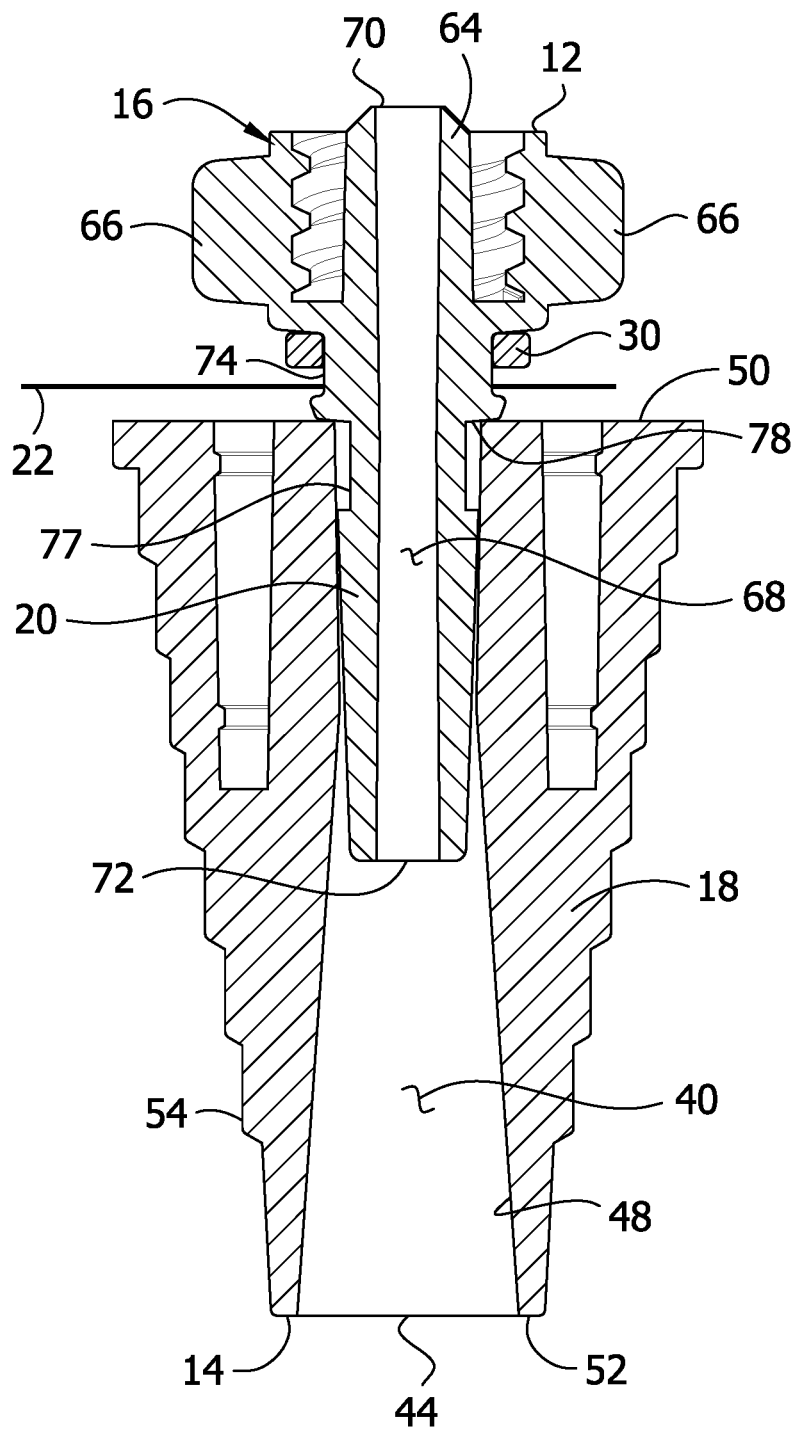
FIG. 3 is a schematic illustration showing a vertical cross-sectional view of the adapter assembly.

Referring to FIGS. 1-3, the adapter assembly 10 comprises a plug 18 (broadly, a connector) and the male fitting 16 releasably coupled with the plug. A mating member 20 may be secured to the male fitting 16 and removably inserted into the plug 18 to attach the male fitting to the plug. Removal of the mating member 20 from the plug 18 can preferably be accomplished without destroying the mating member or the plug. In the illustrated embodiment, the mating member 20 is formed integrally with the male fitting 16. The male fitting 16 and the mating member 20 together may be broadly considered a "connection member," and/or a "subassembly" for use in producing the adapter assembly 10. In the preferred embodiment, the mating member 20 and male fitting 16 may be molded as one plastic piece from a suitable material such as a thermoplastic polymer. However, the mating member 20 could be formed separately from the male fitting 16 and attached to the mating member by a suitable means. The mating member 20 and fitting 16 could also be formed from a material other than plastic. A label 22 may be attached to the male fitting 16. The label 22 may include a warning or notification in the form of indicia 24 alerting a user that the adapter assembly 10 is for use only in enteral feeding and in pharmacies. A cap 26 may be secured to the fitting 16 by a tether 28. The tether may comprise a first ring 30 secured around the mating member 20, a second ring 32 secured around the cap 26, and a cord 34 connecting the first ring to the second ring. The cap 26 may be configured to thread into and seal the male fitting 16 when the adapter assembly 10 is not in use. The cap 26 may include a grip portion 36 for manipulating the cap and a female fitting portion 38 for connecting to the male fitting 16 to cover a top of the male fitting when the adapter assembly 10 is not being used, and to remove the cap for use of the fitting.

Figure 4:
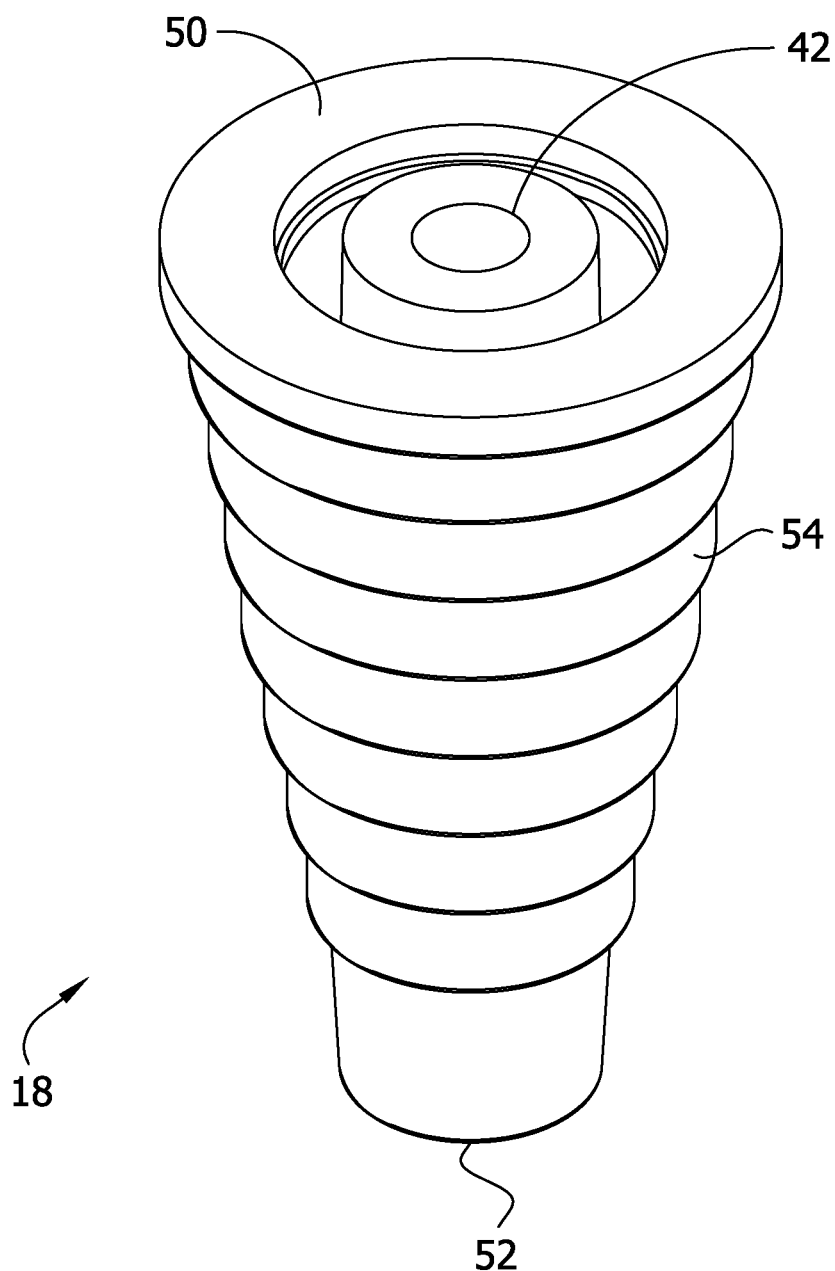
FIG. 4 is a schematic illustration showing a perspective view of a plug of the adapter assembly.
Figure 5:
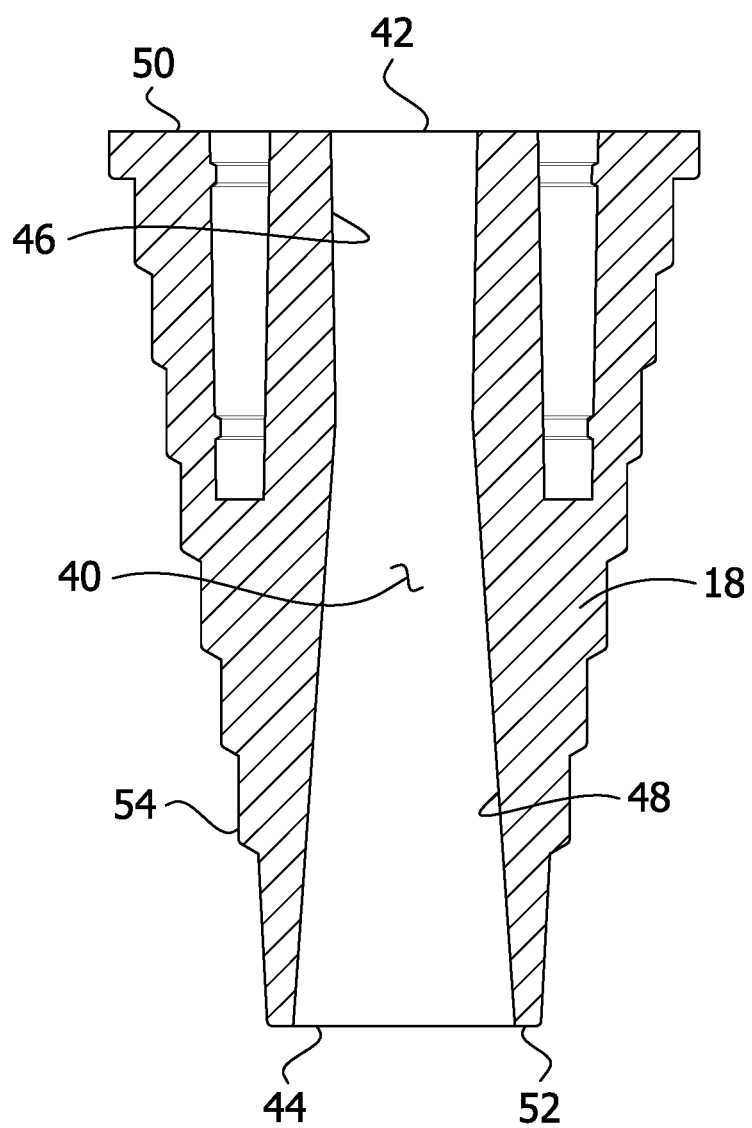
FIG. 5 is a schematic illustration showing a vertical cross-sectional view of the plug.

Referring to FIGS. 4 and 5, the plug 18 may comprise a central passage 40 extending between top and bottom openings 42, 44. The central passage 40 may include a first section 46 adjacent the top opening 42 and a second section 48 adjacent the bottom opening 44. The first section 46 may have constant diameter along a length of the first section and the second section 48 may have a diameter that tapers from the bottom opening 44 toward the first section. An outer diameter of the plug 18 may taper from a top 50 of the plug to a bottom 52 of the plug. An outer surface 54 of the plug 18 may have a stepped configuration. The tapered diameter and stepped configuration of the plug 18 can facilitate insertion of the plug into bottles, tubes or other suitable medical conduits having openings of different diameters. The plug 18 can be formed from rubber, plastic, or any other suitable material for making a liquid seal.

Figure 6:
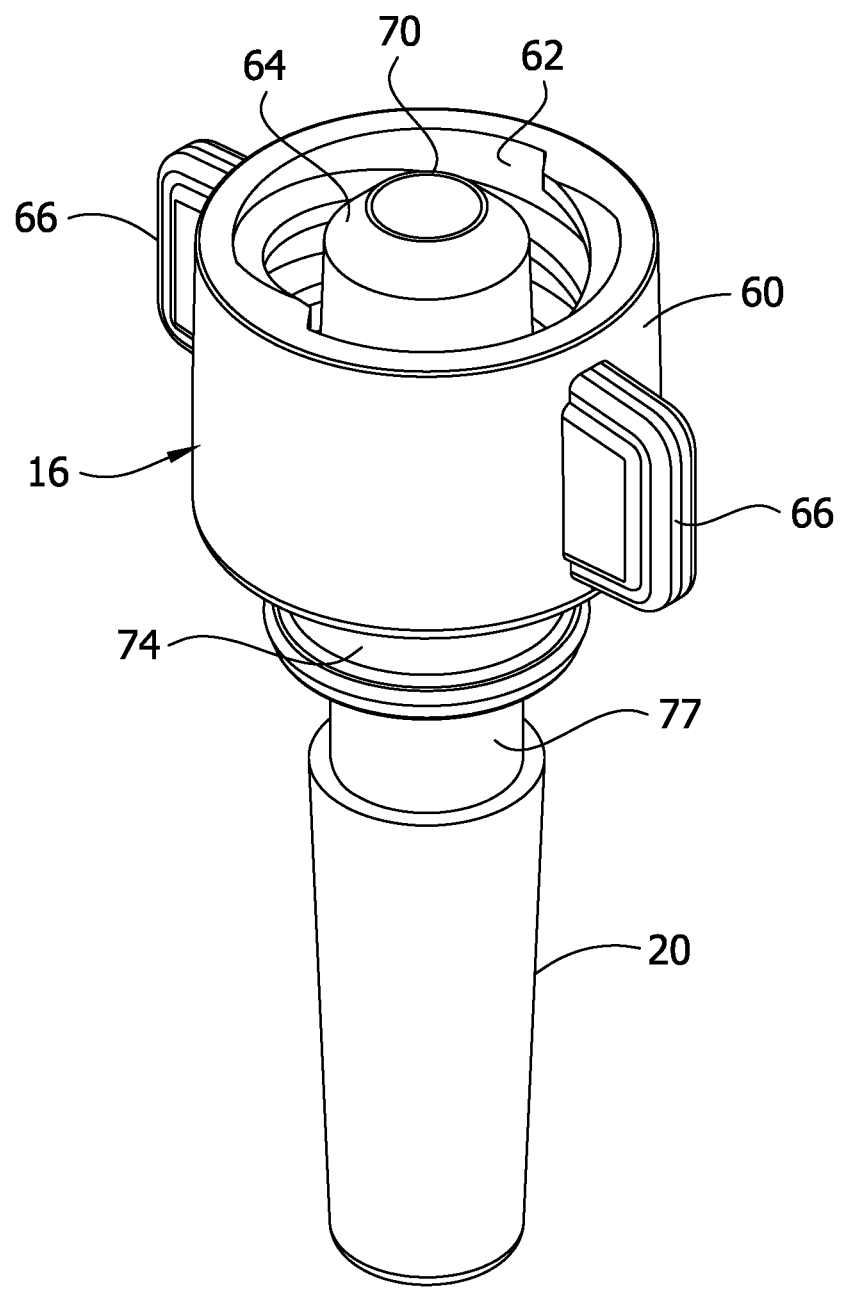
FIG. 6 is a schematic illustration showing a perspective view of a fitting and mating member of the adapter assembly.
Figure 7:
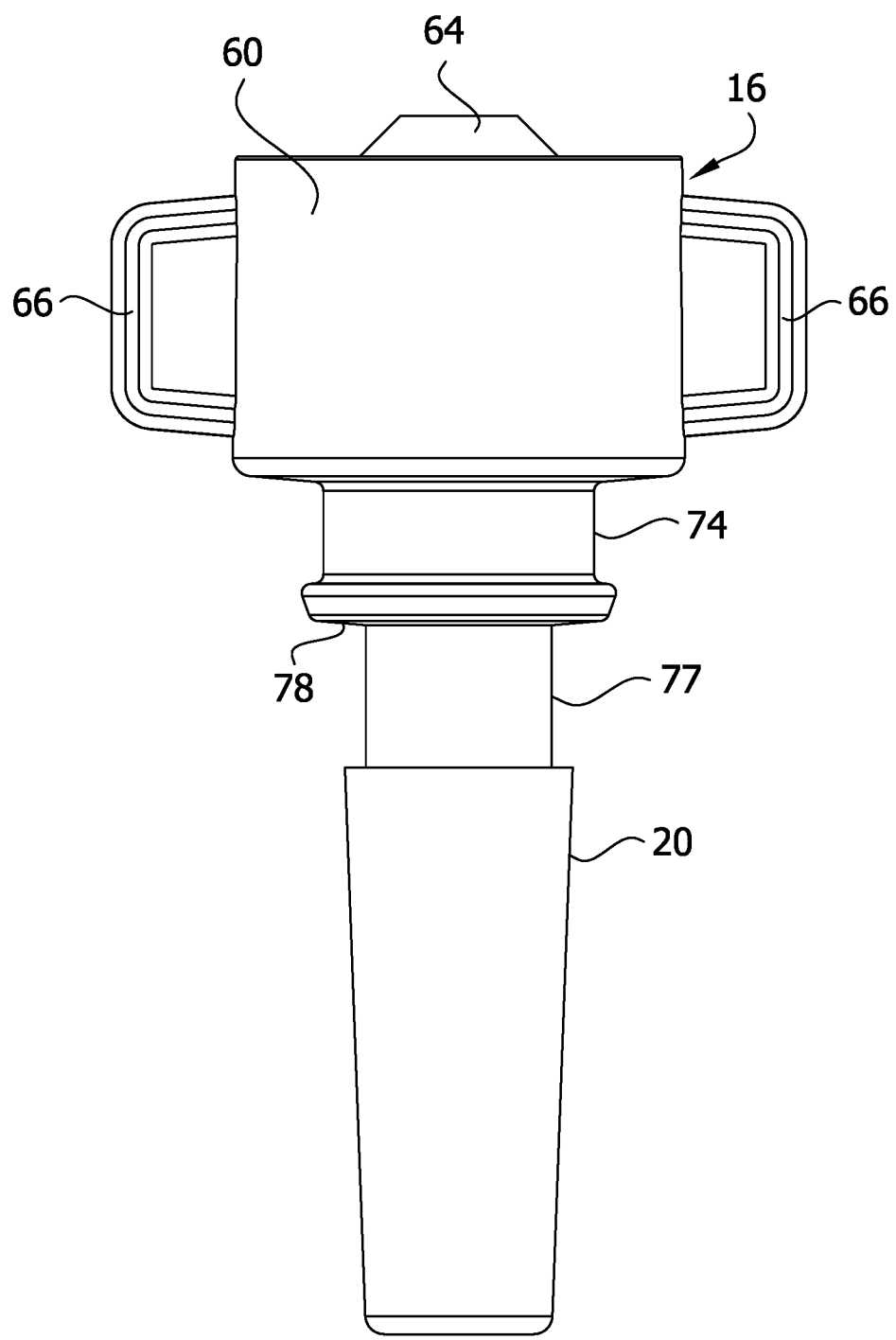
FIG. 7 is a schematic illustration showing a front elevational view of the fitting and mating member.
Figure 8:
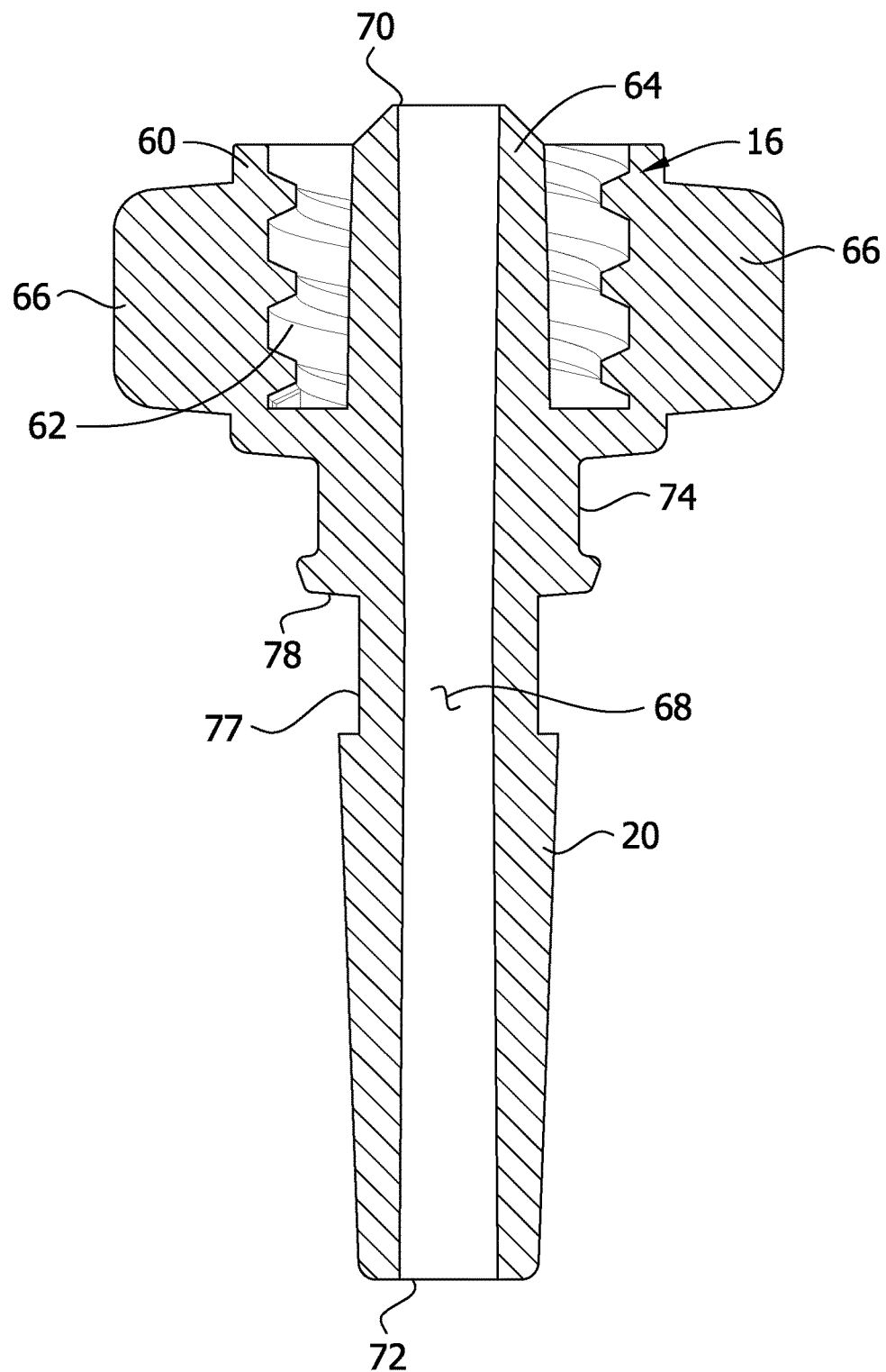
FIG. 8 is a schematic illustration showing a vertical cross-sectional view of the fitting and mating member.

Referring to FIGS. 6-8, the male fitting 16 typically includes an annular portion 60 having a threaded inner surface 62 and a tubular portion 64 disposed at least partially within the annular portion. The threaded inner surface 62 and an outer surface of the tubular portion 64 are configured to engage a female fitting for connecting the adapter assembly 10 to an enteral feeding element. Wings 66 on the male fitting 16 facilitate rotation of the male fitting when it is to be engaged or disengaged with the female fitting. In the illustrated embodiment, the wings 66 are disposed on opposite sides of the male fitting 16. The exemplarily illustrated embodiment depicts a pair of wings oppositely disposed about the fitting 16 however a plurality of wings may utilized, e.g., equispatially disposed around the fitting 16. A central passage 68 (FIG. 8) extends through the male fitting 16 and the mating member 20 integrally formed with the male fitting. The central passage 68 extends between an inlet 70 of the male fitting 16 and an outlet 72 of the mating member 20. In one embodiment, the connection member (male fitting 16 and mating member 20) may have an overall length of about 33.1 mm and the central passage may have a diameter of about 2.8 mm. The outer diameter of the tubular portion 64 may be about 5.41 mm, and the outer diameter of the annular portion 60 (not including wings 66) may be about 12.2 mm. The mating member 20 may taper from a widest portion (nearest male fitting 16) to a narrowest portion (remote from male fitting 16). In one embodiment, the widest outer diameter of the mating member 20 may be about 6.2 mm and the narrowest portion may be about 5.1 mm. It will be understood that the dimensions are exemplary only and that the connection member may have other dimensions within the scope of the present invention.

An annular channel 74 formed in an outer surface of the mating member 20 is configured to receive the first ring 30 of the tether 28 for securing the tether to the mating member and male fitting 16. The annular channel 74 may also secure the label 22 to the mating member 20 and male fitting 16. In the illustrated embodiment, the label 22 comprises a planar member and has a hole 76 for receiving the mating member 20 (FIG. 2). The label 22 can be slid along the mating member 20 until the hole 76 is in registration with the annular channel 74. The engagement between a rim of the hole 76 and the annular channel 74 retains the label 22 on the mating member 20 and male fitting 16. Another annular channel 77 is formed in the outer surface of the mating member 20 below annular channel 74.

In one embodiment, the adapter assembly 10 may be formed by providing the stepped and tapered plug 18 having the central passage 40, and the tapering and stepped outer surface 54. A subassembly may be formed that includes the fitting 16 connected to the mating member 20. The fitting 16 and mating member 20 can be made by molding them out of one piece of material, such as plastic. The subassembly can be coupled with the plug 18 by inserting the mating member 20 into the central passage 40 of the plug. The insertion may be such that the mating member 20 is substantially entirely disposed out of sight within the plug 18. The insertion produces a sealing, interference fit of the mating member 20 with the plug 18. As a result, there is a sealed passage extending from the male fitting 16 through the plug 18 providing fluid communication through the adapter assembly 10. The interference fit of the mating member 20 in the plug 18 is configured so that the mating member 20 can be nondestructively removed from the plug.

Referring back to FIG. 3, for assembling or coupling, the mating member 20 is inserted into the top opening 42 of the plug 18 such that the outlet 72 directly communicates with the second section 48 of the central passage 40 in the plug. A shoulder 78 formed on the mating member 20 may be configured to engage the top 50 of the plug 18 to seat the male fitting 16 on the plug. The mating member 20 may be received in the central passage 40 of the plug 18 by a liquid-tight, interference fit. Thus, in some cases, the plug 18 can be comprised of a deformable or resilient material, such as an elastomeric material, to accommodate or facilitate creation of an interface between an outer portion of the plug and an opening, e.g., mouth, of the reservoir or vessel, or bottle containing the fluid to be delivered. Thus, in a non-limiting example, the plug 18 can be comprised of a thermoplastic elastomer having a hardness in a range of from about 35 to about 75 Shore A durometer. In one particular embodiment, the plug is comprised of a block copolymer of styrene and butadiene, or of styrene and ethylene/butylene, each of which is commercially available from Kraton Polymers US LLC, Houston, Tex.

In use, the adapter assembly 10 places an enteral feeding fluid source having a female fitting in fluid communication with a fluid conduit to deliver fluid to the fluid conduit. Alternatively, the adapter assembly 10 can place an enteral fluid retrieval device (e.g., a syringe) having a female fitting in fluid communication with a fluid reservoir (e.g., bottle) for retrieving fluid from the fluid reservoir. Thus, the adapter assembly 10 adapts a female fitting for compatible connection with a standard feeding tube port or bottle. In the case of fluid delivery to a fluid conduit, fluid from the fluid source flows past the inlet 70 of the male fitting 16, through the central passage 68 in the male fitting and mating member 20 and out the outlet 72 of the mating member into the second section 48 of the central passage 40 in the plug 18. The fluid may then flow out of the bottom opening 44 in the plug 18 and into the fluid conduit.

In some configurations, each of the male fitting portions and the female fitting portions is sized and configured to conform to the requirements under AAMI/ISO 80369-3, titled Small-bore connectors for liquids and gases in healthcare applications—Part 3: Connectors for enteral applications, which is incorporated herein by reference in its entirety for all purposes, including the general requirements at parts 4, dimension requirements at part 5, and performance requirements at part 6 thereof.

Having described embodiments of the invention in detail, it will be apparent that modifications and variations are possible without departing from the scope of the invention defined in the appended claims.

When introducing elements of the present invention or the preferred embodiments thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

The invention claimed is:

1. An adapter assembly comprising:
a tapered connector including a central passage and a tapered outer surface for sealing openings of different sizes in at least one of a tube and a bottle;
a male fitting coupled with the tapered connector and in fluid communication with the central passage for attaching a device having a complementary fitting to the tapered connector, the male fitting including an annular portion having a threaded inner surface and a tubular portion disposed at least partially within the annular portion; and
a mating member formed on a distal end of the male fitting such that the mating member and male fitting are formed as one piece of material, the mating member including a shoulder formed on the mating member and projecting outwardly from a remainder of the mating member in a transverse direction a distance less than a distance the annular portion projects in the transverse direction, the mating member further comprising a tapered section, and an outer surface annular channel located between the shoulder and the tapered section of the mating member, the outer surface annular channel being recessed from at least a portion of the tapered section and being free of threads therein;
wherein the tapered outer surface of the tapered connector comprises a multi-stepped configuration including at least three steps.

2. The adapter assembly set forth in claim 1 further wherein the male fitting is releasably coupled with the connector.

3. The adapter assembly as set forth in claim 1 wherein the tapered connector is comprised of a thermoplastic polymer having a Shore A hardness in a range of from about 35 to about 75.

4. The adapter assembly set forth in claim 1 wherein the mating member is removably received in the central passage of the connector.

5. The adapter assembly set forth in claim 1 further comprising a cap secured to the male fitting, the cap comprising a female fitting complementary to the male fitting coupled with the connector.

6. The adapter assembly set forth in claim 5 further comprising a tether securing the cap to the male fitting.

7. The adapter assembly set forth in claim 1, further comprising a label connected to the adapter assembly.

8. The adapter assembly set forth in claim 1 wherein the tapered connector is comprised of an elastomeric material having a Shore A hardness in a range of from about 35 to about 75, wherein the male fitting comprises a mating member, and wherein the central passage is sized to resiliently form a seal around the mating member.

9. The adapter assembly set forth in claim 1, wherein the outer surface annular channel comprises a first outer surface annular channel, the assembly further comprising a second outer surface annular channel located between the shoulder and the annular portion of the male fitting, a section of the mating member defining the second outer surface annular channel having a width that is greater than a width of a section of the mating member defining the first outer surface annular channel.

10. The adapter assembly as set forth in claim 1 wherein the shoulder extends around an entire circumference of the mating member.

11. The adapter assembly set forth in claim 1, wherein a distal end of the tubular portion is tapered.

* * * * *